(12) United States Patent
Battefeld et al.

(10) Patent No.: US 7,799,202 B2
(45) Date of Patent: Sep. 21, 2010

(54) METHOD FOR DETERMINING PARAMETERS OF A GAS-SELECTIVE ELECTRODE

(75) Inventors: Manfred Battefeld, Duesseldorf (DE); Klaus Bittner, Krefeld (DE); Andreas Golitz, Moers (DE); Markus Hahn, Kempen (DE); Michael Kussmann, Duesseldorf (DE); Aurelia Stellmach-Hanulok, Wuelfrath (DE)

(73) Assignee: Hach Lange GmbH, Berlin (DE)

( * ) Notice: Subject to any disclaimer, the term of this patent is extended or adjusted under 35 U.S.C. 154(b) by 1450 days.

(21) Appl. No.: 11/195,010

(22) Filed: Aug. 2, 2005

(65) Prior Publication Data

US 2006/0027464 A1 Feb. 9, 2006

(30) Foreign Application Priority Data

Aug. 3, 2004 (EP) .................................. 04018344

(51) Int. Cl.
 $G01N\ 27/31$ (2006.01)
(52) U.S. Cl. .................... 205/780.5; 205/775; 204/432; 73/1.06; 702/23
(58) Field of Classification Search ................ 204/416, 204/417, 431, 432; 205/775, 780.5; 700/2; 702/22, 23; 73/1.06
See application file for complete search history.

(56) References Cited

U.S. PATENT DOCUMENTS

| 5,016,201 A | 5/1991 | Bryan et al. ............. 364/571.4 |
| 5,046,028 A | 9/1991 | Bryan et al. ................. 364/550 |
| 5,098,547 A * | 3/1992 | Bryan et al. ................. 204/401 |
| 5,139,626 A * | 8/1992 | Yamaguchi et al. ...... 205/778.5 |
| 5,266,179 A * | 11/1993 | Nankai et al. ............... 204/401 |
| 5,376,255 A * | 12/1994 | Gumbrecht et al. ......... 204/426 |
| 5,580,441 A | 12/1996 | Amemiya et al. ........... 205/789 |
| 5,976,465 A * | 11/1999 | Luzzana et al. .......... 204/403.1 |
| 5,985,117 A * | 11/1999 | Bachas et al. ............... 204/418 |

FOREIGN PATENT DOCUMENTS

| DE | 39 37 635 C2 | 5/1991 |
| EP | 0 667 522 B1 | 8/1995 |
| GB | 1535361 | 12/1978 |
| JP | 6-130030 | 5/1994 |

OTHER PUBLICATIONS

Bakker, Eric. "Selectivity comparison of neutral carrier-based ion-selective optical and potentiometric sensing schemes." Analytica Chamica Acta, 350, 1997. pp. 329-340.*

* cited by examiner

*Primary Examiner*—Kaj K Olsen
(74) *Attorney, Agent, or Firm*—Fay Sharpe LLP

(57) ABSTRACT

Gas-selective electrodes in liquid analyzing devices have a characteristic curve K with a linear portion L and a non-linear portion NL. In the non-linear portion NL, the characteristic previously could only be estimated so that determinations of the concentration were rather inexact. According to the present application, the electrode is rinsed with an acid and the zero point voltage $U_N$ at the electrode is determined during the rinsing. Using the zero point voltage $U_N$, the non-linear portion NL of the characteristic K is determined with high precision so that even low concentrations c can be determined with great accuracy.

11 Claims, 2 Drawing Sheets

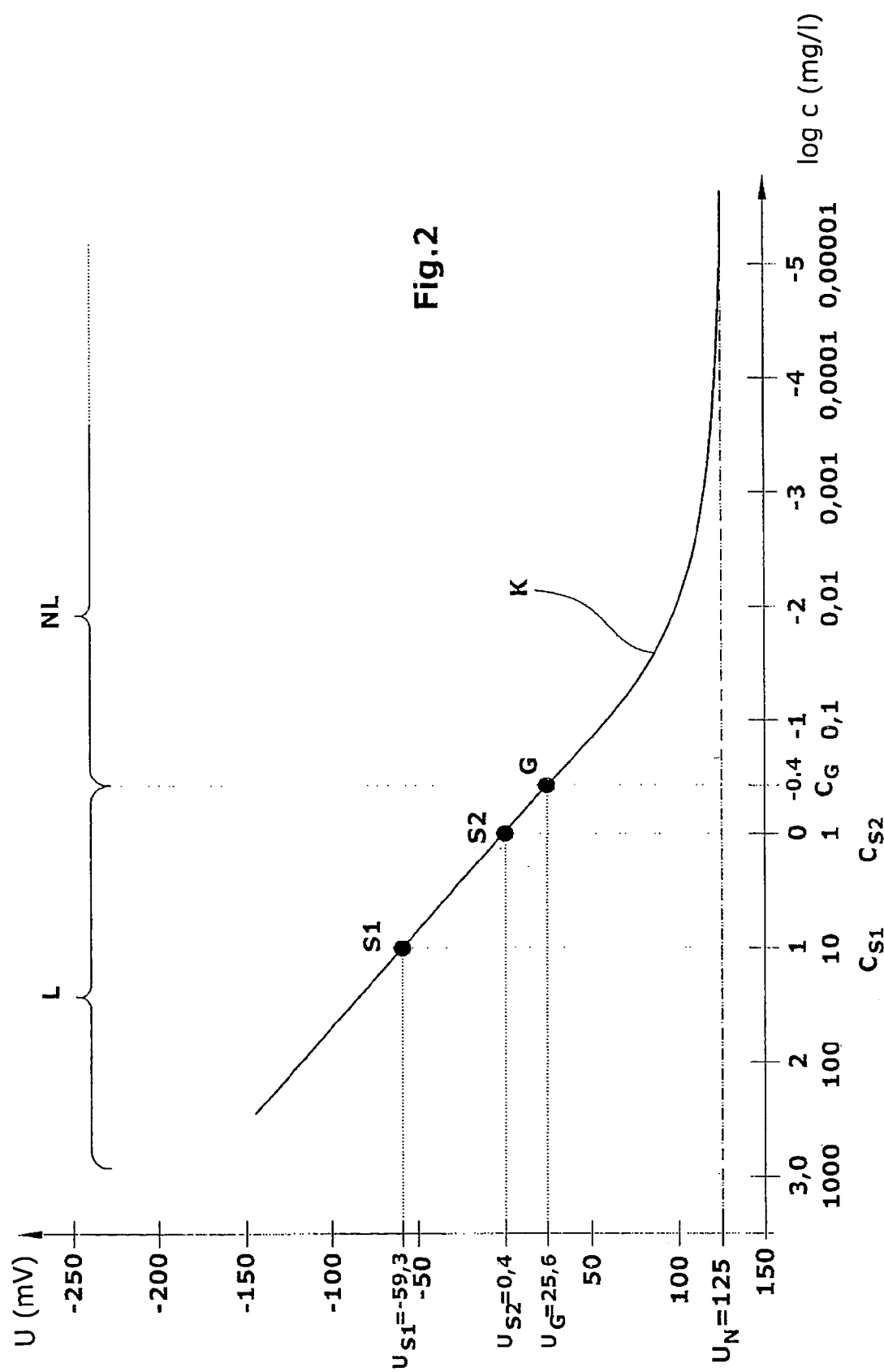

METHOD FOR DETERMINING PARAMETERS OF A GAS-SELECTIVE ELECTRODE

BACKGROUND OF THE INVENTION

1. Field of the Invention

The invention refers to a method for determining parameters of a characteristic of a gas-selective electrode in an automatic liquid analyzing device.

2. Related Prior Art

Automatic liquid analyzing devices with a gas-selective electrode are used, for example, to determine the content of ammonium in waste water. The concentration/voltage characteristic of gas-selective electrodes is always plotted logarithmically. The logarithmic characteristic of gas-selective electrodes typically is linear in the range of medium and high concentrations so that the position and the inclination of the linear portion of the characteristic can be determined by measurements using two standard solutions of different concentration. With concentrations below a limit value, the characteristic is not linear but becomes ever flatter as the concentration decreases. Determining or estimating the non-linear portion of the characteristic is effected by measurements using further standard solutions. This method is cumbersome and, moreover, inexact.

Spent gas-selective electrodes supply inexact measuring results. The degree of electrode wear can only be determined by evaluating the measuring results obtained with the standard solutions, which is inexact.

It is an object of the invention to improve the precision of measurement for measurements taken with a gas-selective electrode in an automatic liquid analyzing device.

SUMMARY OF THE INVENTION

According to the invention, the gas-selective electrode is rinsed with an acid. During the rinsing, the zero point voltage $U_N$ is determined at the gas-selective electrode. The voltage value at the electrode is stored as the zero point voltage $U_N$ as soon as the voltage has stabilized during the rinsing.

The acid removes carbonates and other contaminations from the gas-selective electrode and quickly expels measurement gas. Thus, a measurement gas concentration of almost zero at the electrode is quickly obtained so that a constant zero point voltage can be determined at the electrode after a very short period, i.e. after a few minutes at the latest.

Suitable rinsing acids are acids which, among others, contain no outgassing components. In particular, hydrochloric acid is unsuitable since it would interfere with the electrode function.

Using the method described, the zero point voltage $U_N$ of the gas-selective electrode can be determined at any time. Therefore, the method is extraordinarily well suited to be carried out in regular intervals and automatically. This allows to draw several conclusions which, among others, allow for more exact measurement results in the range of small gas concentrations.

Preferably, the rinsing is effected during an automatic cleaning of the analyzing device. In continuous operation of the liquid analyzing device, a regular cleaning of the wet part of the analyzing device is necessary. The electrode is rinsed during the cleaning of the analyzing device so that no measuring time is wasted for rinsing and determining the zero point voltage of the gas-selective electrode.

Preferably, following the determination of the zero point voltage, a depletion signal is generated when the zero point voltage reaches or exceeds a predetermined depletion voltage value. The zero point voltage of the electrode is a reliable parameter for determining the depletion of the gas-selective electrode. In this manner, it is reliably avoided that erroneous measurements are inadvertently made with a depleted or spent electrode.

Preferably, the electrode is an ammonia electrode for determining the ammonium content in waste water. The rinsing acid may be citric acid. Generally, it may also be any other gas-selective electrode that is cleaned with an acid.

According to a preferred embodiment, the non-linear portion of the characteristic of the gas-selective electrode is determined by interpolation of the characteristic between its linear portion and the zero point defined by the zero point voltage, using an exponential function. The non-linear portion of the electrode characteristic can be represented with sufficient certainty by an exponential function. Since a relatively exact electrode characteristic can be determined in the non-linear portion, gas concentrations below a limit concentration, i.e. below the gas concentration where the characteristic passes from its linear portion to the non-linear portion, can also be determined with an exactness better than 10%.

Preferably, for $c <= c_G$, the interpolation is performed according to the function $$U = U_N (1 - e^{(E/U_N(\log c - F))})$$

where

U is the electrode voltage, $U_N$ is the zero point voltage of the electrode,

E is a constant quantifying the curvature of the exponential function, c is the concentration of the measuring gas, $c_G$ is the limit concentration, and F is the position of the exponential function on the concentration axis.

By means of the requirements that the linear and the non-linear portions of the characteristic transition at a limit point G, and the transition at the limit point is always differentiable, and the function $$U = x \log c + y \text{ for } c >= c_G$$

as well as by determining x and y by two measurements with standard solutions and by determining the zero point voltage $U_N$, three of the four variables $U_N$, E, F and $c_G$ can be determined. Only the limit point concentration $c_G$ or the constant of curvature E remains undetermined and has to be set.

Preferably, the constant of curvature E is set. The constant of curvature E is specific to an electrode and is determined empirically. The constant of curvature E can be determined exactly such that the error in the non-linear portion of the characteristic thus obtained is less than 10%, generally even less than 5%.

Merely by determining the zero point voltage $U_N$ during the rinsing or cleaning interruption, the measuring range of a gas-selective electrode can be expanded to low gas concentrations in the non-linear portion of the characteristic, realizing a high determination accuracy in the non-linear portion of the characteristic. This method is generally applicable to all electrodes and is not restricted to gas-selective electrodes.

BRIEF DESCRIPTION OF THE DRAWINGS

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 2 is a graph showing a characteristic K of a gas-selective electrode of the analyzing device.

DETAILED DESCRIPTION OF A PREFERRED EMBODIMENT

Figure 1:
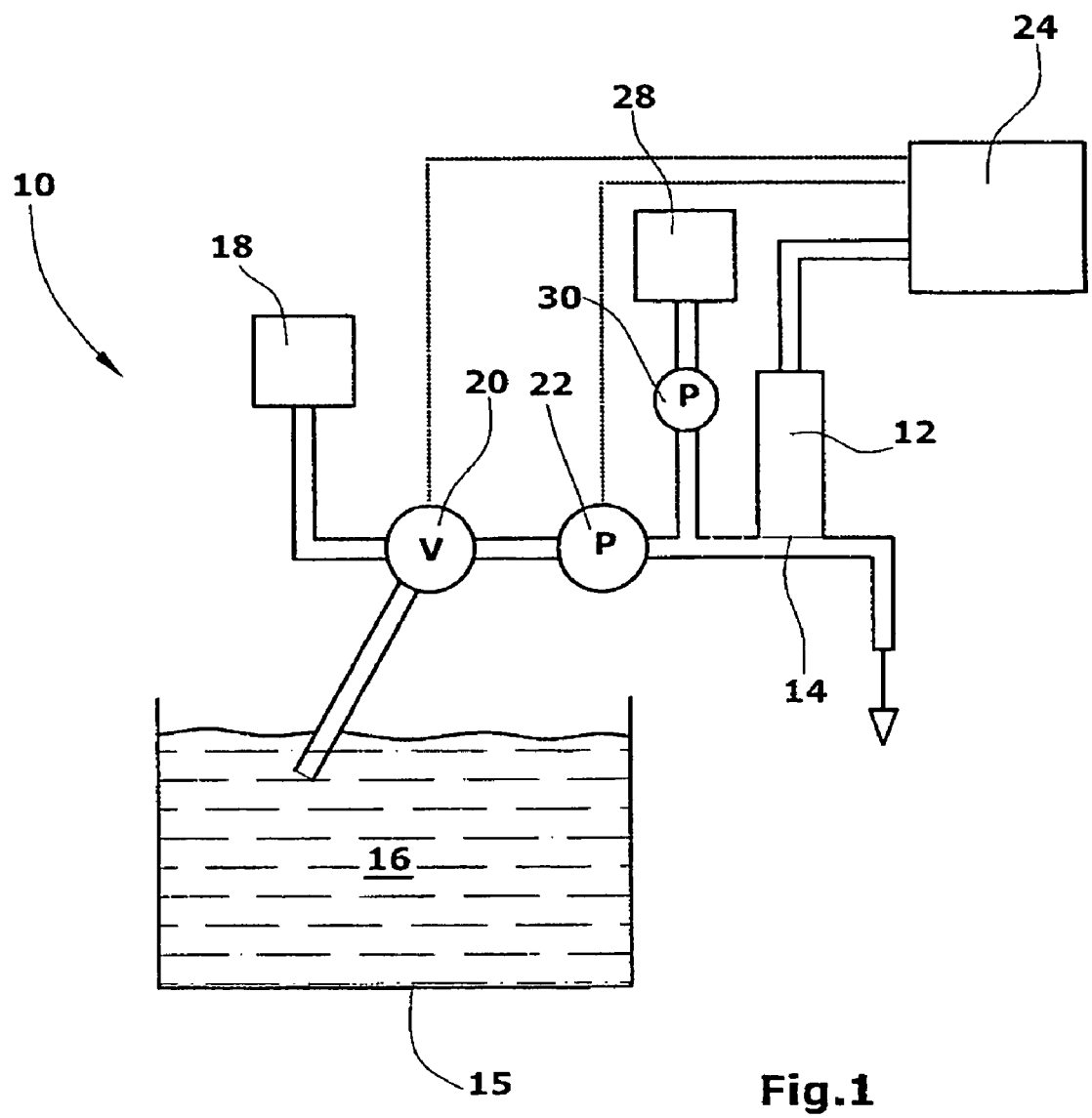
FIG. 1 is a schematic representation of a liquid analyzing device according to the present invention.

FIG. 1 is a schematic and simplified illustration of a liquid analyzing device 10. In the present case, the liquid analyzing device 10 serves to determine the presence of ammonium in waste water. The analyzing device 10 substantially comprises a gas-selective electrode 12, a pump 22, a three-way valve 20, an acid container 18, a sodium hydroxide container 28, a sodium hydroxide pump 30, as well as a control device or processor 24 for controlling the pumps 22, and the valve 20 and for evaluating the voltage signals from the electrode 12.

In measurement operation, the pump 22 pumps waste water 16 from a waste water reservoir 15 towards the electrode 12. Further, the pump 30 pumps sodium hydroxide from the container 28 into the waste water pumped towards the electrode 12. The sodium hydroxide causes an alkaline shift in the pH value of the waste water which turns the ammonium turning into ammonia. In the area of the electrode 12, the ammonia passes through a gas-selective membrane 14 so that the electrode 12 generates a voltage signal corresponding to the ammonia content of the waste water, which is evaluated by the control device 24.

The analyzing device 10 is automatically cleaned and the electrode 12 rinsed in regular intervals. To do so, the control device 24 switches the valve 20 such that acid, for example citric acid, is pumped from the acid container 18 through the pump 22 along the electrode 12. The electrode 12 is cleaned by the acid of carbonates and other contaminations and ammonia is very quickly expelled from the electrode 12. In the process, a zero point voltage $U_N$ appears at the electrode 12, which is measured and stored by the control device 24.

Further containers with two standard solutions may be provided, with which two calibration points $S_1$, $S_2$ of the characteristic curve K shown in FIG. 2 can be determined in a linear portion L thereof.

In the diagram of FIG. 2, the electrode voltage U in millivolts (mV) is plotted versus the logarithm of the concentration log c in milligrams per liter (mg/l) and it shows the characteristic curve K of the gas-selective electrode 12. The characteristic curve K has the linear portion L for medium and high concentrations and a non-linear portion NL for low concentrations. From the two standard measuring points $S_1$ and $S_2$, the linear portion L of the electrode characteristic curve K is determined and stored in the control device 24.

Further, a predetermined constant of curvature E is stored in the control device 24.

For $c <= c_G$, the interpolation of the non-linear portion NL is performed according to the function $$U = U_N(1 - e^{(E/U_N)(\log c - F)})$$

where

U is the electrode voltage,
$U_N$ is the zero point voltage of the electrode,
E is a constant quantifying the curvature of the exponential function,
c is the concentration of the measuring gas,
$c_G$ is the limit concentration, and
F is the position of the exponential function on the concentration axis.

By means of the requirements that
the linear and the non-linear portions of the characteristic transition at a limit point G, and
the transition at the limit point is always differentiable, and the function $$U = x \log c + y \text{ for } c >= C_c$$

and the predetermined constant of curvature E, the limit point concentration $c_G$ can be determined and substituted in the function for the non-linear portion NL.

The constant of curvature E is specific to the electrode and is determined empirically. The constant of curvature E can be determined so exactly that the error in the non-linear portion of the characteristic thus determined is less than 10%, generally even less than 5%.

In the exemplary diagram of FIG. 2, the standard solution $S_1$ has an ammonium concentration of 10 mg/l and the standard solution $S_2$ has an ammonium concentration of 1.0 mg/l. The calibration measurements showed a voltage $U_{S1}$ of −59.3 mV for $S_1$ and a voltage $U_{S2}$ of 0.4 mV for $S_2$.

From the voltages $U_{S1}$ and $U_{S2}$, the following is obtained for the linear portion L for $c >= c_c$:

$$U = \log c + y \text{ with } x = -59.7 \text{ mV and } y = 0.35 \text{ mV.}$$

125.0 mV were measured as the zero point voltage $U_N$.

A value of 75.0 mV/log c was set for the curvature E.

In the present example, the control device 24 calculated a value of 0.4 mg/l for the limit concentration so that log $c_G = 0.4$. The limit voltage $U_G$ thus is 25.6 mV.

Thus, the non-linear portion NL is described entirely so that measurements of lower concentrations can also be performed with sufficiently high accuracy.

The depletion value for the electrode is stored as 100 mV. When the zero point voltage $U_N$ reaches this value, a depletion signal is outputted.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for determining parameters of a characteristic curve of a gas-selective electrode in an automatic liquid analyzing device, the method comprising the following steps:
   rinsing the electrode with an acid, and
   determining a zero point voltage $U_N$ present at the electrode during the acid rinsing, wherein a depletion signal is output when the zero point voltage $U_N$ reaches a predetermined depletion value.

2. The method of claim 1, wherein the acid rinsing is performed during an automatic cleaning of the electrode.

3. The method of claim 1, wherein the electrode is an ammonia electrode.

4. The method of claim 1, wherein the rinsing acid is citric acid.

5. The method of claim 1, further including:
   determining a non-linear portion NL of the characteristic curve K of the electrode by interpolating the characteristic curve K between a linear portion L and the zero point voltage $U_N$ according to an exponential function.

6. The method of claim 5, wherein the exponential interpolation function is:

$$U=U_N(1-e^{(E/U_N(\log c - F))})$$

where
- U is an output electrode voltage,
- $U_N$ is the zero point voltage of the electrode,
- E is a constant quantifying the curvature of the exponential function,
- c is a concentration of the measuring gas,
- the linear and the non-linear portions L, NL of the characteristic curve K transition at a limit point G,
- $c_G$ is a limit concentration at the limit point G,
- F is a position of the exponential function on a concentration axis,
- the transition at the limit point G is differentiable, and
- at least one of the limit point concentration $c_G$ and the constant of curvature E is fixed.

7. The method of claim 6, wherein the constant of curvature E is fixed.

8. An apparatus for performing the method of claim 1.

9. An automatic liquid sample analysis device comprising:
- a gas-selective electrode;
- a means for rinsing the electrode with an acid;
- a control processor for determining a characteristic curve K of the gas-selective electrode, the control processor being programmed to:
  - determine a zero point voltage $U_N$ present at the gas-selective electrode during an acid rinse; and
  - output a depletion signal in response to the zero point voltage $U_N$ reaching a predetermined depletion value.

10. The apparatus of claim 9 wherein the processor is further programmed to:
- determine a non-linear portion NL of the characteristic curve K between a linear portion L and the zero point voltage $U_N$ by interpolating with the interpolation function:

$$U=U_N(1-e^{(E/U_N(\log c - F))})$$

where
- U is an output electrode voltage, $U_N$ is the zero point voltage of the gas-selective electrode,
- E is a electrode specific constant of curvature of the exponential function,
- c is a concentration of the measuring gas,
- the linear and the non-linear portions L, NL of the characteristic curve K transition at a limit point G,
- $c_G$ is a limit concentration at the limit point G,
- F is a position of the exponential function on a concentration axis,
- a transition at the limit point G is differentiable, and
- at least one of the limit point concentration $c_G$ and the constant of curvature E is fixed.

11. The apparatus of claim 9 wherein the processor is further programmed to:
- determine a concentration from an output of the gas-selective electrode after the acid rinsing and during sampling of a sample using the determined concentration curve K.

* * * * *